(12) United States Patent
Mabritto et al.

(10) Patent No.: US 8,993,040 B2
(45) Date of Patent: Mar. 31, 2015

(54) METHOD AND APPARATUS FOR DEPOSITING A BIOLOGICAL FLUID ONTO A SUBSTRATE

(75) Inventors: Giacomo Mabritto, Arnad (IT); Cristina Panciatichi, Arnad (IT); Oriana Rossotto, Arnad (IT); Tazio Sandri, Arnad (IT)

(73) Assignee: Sicpa Holding SA, Prilly (CH)

( * ) Notice: Subject to any disclaimer, the term of this patent is extended or adjusted under 35 U.S.C. 154(b) by 370 days.

(21) Appl. No.: 13/266,913

(22) PCT Filed: Apr. 29, 2009

(86) PCT No.: PCT/EP2009/055227
§ 371 (c)(1),
(2), (4) Date: Oct. 28, 2011

(87) PCT Pub. No.: WO2010/124734
PCT Pub. Date: Nov. 4, 2010

(65) Prior Publication Data
US 2012/0050411 A1    Mar. 1, 2012

(51) Int. Cl.
*B41J 2/015* (2006.01)
*B41J 2/05* (2006.01)
*B05D 3/10* (2006.01)
*B01L 3/02* (2006.01)
*B41J 2/045* (2006.01)
*G01N 35/10* (2006.01)

(52) U.S. Cl.
CPC ........... *B01L 3/0268* (2013.01); *B41J 2/04513* (2013.01); *B41J 2/04555* (2013.01); *B41J 2/0458* (2013.01); *B01L 2200/141* (2013.01); *B01L 2300/0681* (2013.01); *B01L 2300/0861* (2013.01); *B01L 2400/0442* (2013.01); *G01N 2035/1041* (2013.01)

USPC ................ 427/2.1; 427/2.12; 347/20; 347/56

(58) Field of Classification Search
USPC .............................. 427/2.1, 2.12; 347/20, 56
See application file for complete search history.

(56) References Cited

U.S. PATENT DOCUMENTS 6,315,381 B1 * 11/2001 Wade et al. ...................... 347/19
6,395,494 B1 * 5/2002 Grainger et al. ................ 435/7.1
6,460,974 B1 * 10/2002 Lebron ............................ 347/55

(Continued)

FOREIGN PATENT DOCUMENTS

EP           1093918 A2     4/2001

OTHER PUBLICATIONS

International Search Report of PCT/EP2009/055227 Dated Apr. 7, 2010.

*Primary Examiner* — Cachet Sellman
(74) *Attorney, Agent, or Firm* — Greenblum & Bernstein, P.L.C.

(57) ABSTRACT

There is described a method for depositing at least one biological fluid onto a surface of a substrate, the method comprising the steps of (i) providing at least one thermal bubble jet printhead loaded with at least one biological fluid, (ii) positioning the printhead next to the substrate, and (iii) supplying the printhead with energy thereby depositing the biological fluid onto the surface. The printhead is supplied with an energy E such that $$E > 1.6 * E_{th}$$

where $E_{th}$ is the threshold energy of the printhead. There are also described an apparatus for depositing at least one biological fluid onto a surface of a substrate and a microarray obtained by carrying out the depositing method.

17 Claims, 6 Drawing Sheets

(56) References Cited

U.S. PATENT DOCUMENTS

| | | | |
|---|---|---|---|
| 7,128,398 B2 * | 10/2006 | DaQuino et al. | 347/49 |
| 2002/0029722 A1 * | 3/2002 | Shioya et al. | 106/31.43 |
| 2002/0113840 A1 * | 8/2002 | Trauernicht et al. | 347/47 |
| 2003/0027219 A1 * | 2/2003 | Ilsley et al. | 435/7.9 |
| 2003/0064052 A1 * | 4/2003 | Waters et al. | 424/85.2 |
| 2003/0198967 A1 * | 10/2003 | Matson et al. | 435/6 |

\* cited by examiner

METHOD AND APPARATUS FOR DEPOSITING A BIOLOGICAL FLUID ONTO A SUBSTRATE

TECHNICAL FIELD

The present invention relates to a method and an apparatus for depositing a biological fluid onto the surface of a substrate. In particular, the present invention relates to a method and an apparatus for manufacturing a microarray. The invention also relates to a microarray obtained with the above cited method and apparatus.

BACKGROUND ART

In the field of the clinical and biochemical analysis, there is an increasing interest in the use of microarrays.

A microarray comprises a substrate made of a suitable material, e.g. glass, polymer coated glass, plastics, nitrocellulose, and the like, on which a plurality of spots of one or more biological fluids, e.g. proteins, cells, DNA fragments, and similar, are fixed. The size of the substrate is, typically, of about some inches, e.g. one inch by three inches, and the spots fixed thereon usually ranging from about 50 µm to about 300 µm in diameter.

Microarrays are important tools for the biological research, in particular genomics, proteomics, and cell analysis, and they are used for the diagnosis and prevention of a lot of diseases. For example, deoxyribonucleic acid (DNA) and protein microarrays, also called "biochip microarrays" have accelerated the process of understanding gene and protein functions in living organisms.

Microarray fabrication is inherently a deposition process of a biological fluid onto a substrate. Very small quantity (nanoliters or picoliters) of one or more biological fluids are deposited onto the substrate in the shape of spots.

For depositing spots, two types of devices are known in the art: "contact printing" devices, e.g. pin printing and microstamping devices, and "non-contact printing" devices, e.g. inkjet-like printing devices, both thermal and piezoelectric.

As it is known, a thermal inkjet printing device comprises a system for feeding a sheet of paper on which an image is to be printed, a carriage driven by a motor in a direction perpendicular to the sheet feeding direction, printing means, typically one or more printheads carried by the carriage and in fluid communication with respective ink reservoirs, and electric power supply means. In particular, each printhead comprises at least one nozzle, typically an array of nozzles, a firing chamber and a heating element.

In use, the electric power supply means supplies energy to the printhead as a pulse electric signal. During each pulse, the heating element warms up of several hundred degrees in few microseconds. A small quantity of ink passes from one of the ink reservoirs to the firing chamber, where it comes into contact with the heating element. Following the contact with the heating element, the ink quickly warms up, thereby generating a vapor bubble inside the firing chamber. The resulting vapor bubble expansion, and the subsequent collapse thereof, cause an ink drop to be ejected through the at least one nozzle of the printhead.

Typically, the thermal inkjet printing devices allow to eject ink drops having a volume ranging from 200 pl to 2 pl, or smaller.

Volume and ejection speed of a drop may vary according to the energy E supplied to the printhead. The threshold energy $E_{th}$ depends on the geometrical characteristics of the printhead, as well as on the thermodynamic and fluidodynamic properties (e.g. boiling point, surface tension, density and viscosity) of the used ink.

It has been experimentally noticed, see for example the U.S. Pat. No. 5,767,872, that for values of the energy E below the threshold energy $E_{th}$ the one or more nozzles of the printhead do not eject any drop. This is because the heating element does not reach a temperature high enough to cause the generation of the vapor bubble. Above the threshold energy $E_{th}$, there is a so called "transitional" or "drop instability" zone, where the drop volume increases with increasing the energy E supplied to the printhead. Above the transitional or drop instability zone there is a so called "drop stability" zone, where the drop volume remains substantially constant with increasing the energy E supplied to the printhead.

In order to guarantee the uniformity of the printed images, the drops ejected through the nozzles should preferably have a constant volume. It is thus advisable the printhead to be operated in the drop stability zone.

Therefore, it is defined as "threshold energy" $E_{th}$ the minimum energy suitable for causing drop ejection through at least one nozzle of a thermal printhead.

Moreover, in the following description, the expression "stable drop" will designate a drop having a constant volume with respect to the energy E supplied to the printhead, whereas the expression "instable drop" will designate a drop having a variable volume with respect to the energy E supplied to the printhead.

However, it has been experimentally observed that if the energy E increases too much with respect to the threshold energy $E_{th}$, although the drop remains stable, the printhead is subjected to a premature ageing, and consequently its lifetime decreases. This is believed to be caused by an excessive warming of the heating element and by the subsequent build-up of ink residues onto the surface thereof. This phenomenon is known with the term of "Kogation".

In fact, the high temperatures reached by the heating element (about 350° C.) cause a degradation of the additives, typically the dyes, present in the ink. Additives are not soluble in the ink, whereby they deposit onto the surface of the heating element, thus forming a proper insulating layer. This insulating layer decreases the thermal efficiency of the heating element and, at the worst, causes the rupture of the printhead.

To obviate the phenomenon of Kogation, and thus to increase the lifetime of a printhead, it is known to supply the printhead with an energy greater than the threshold energy, thereby allowing the ejection of stable drops. However, the energy supplied to the printhead should not be so great to cause the build-up of the insulating layer onto the surface of the heating element. This is disclosed, for example, in the U.S. Pat. Nos. 6,302,507 and 6,315,381, which describe a system and a method for controlling the energy applied to a thermal inkjet printhead assembly.

U.S. Pat. No. 6,575,548 describes a printing system and protocol for providing efficient control of energy characteristics of an inkjet printhead. The printing system includes a controller, a power supply and a printhead assembly having a memory device and a distributive processor integrated with an ink driver. The distributive processor maintains energy characteristics of the printhead assembly within preprogrammed acceptable boundaries. More specifically, the energy supplied to the printhead is approximately 20% over the threshold energy defined above.

U.S. Pat. No. 7,281,783 describes a fluid ejection device comprising a resistor, a chamber, a first fluid channel and a second fluid channel each communicated with the chamber.

To ensure a stable operation, the resistor is supplied with an energy approximately 25 to 50% over the minimum energy or threshold energy.

Thanks to the small amount of liquid dispersed per unit of area and the low production costs of the thermal inkjet printheads, the thermal inkjet printing technique could be employed in the field of the clinical and biomedical analysis. In this case, the ink would be replaced by one or more suitable biological fluids.

U.S. Pat. No. 6,935,727 describes a method for depositing fluids, typically fluids containing a biopolymer or precursor thereof, onto a substrate surface by using a pulse jet printhead assembly. In use, the firing chamber of the printhead assembly is loaded with a volume of fluid that includes a biopolymer or precursor thereof. The loaded printhead assembly is then placed in opposing relation to a surface of a substrate and actuated to deposit a volume of fluid on the substrate.

US patent no. 2003/0027219 describes a method for efficiently depositing small quantities of a protein containing fluid onto the surface of a substrate by using thermal inkjet printing apparatus. The disclosed depositing process does not substantially modulate the protein activity/functionality of the deposited fluid. In practicing the method, a small volume of fluid containing the protein(s) of interest is front loaded into a thermal inkjet device. Next, a small quantity of the front loaded fluid is expelled onto the surface of the substrate.

However, the above cited U.S. Pat. No. 6,935,727 and 2003/0027219 do not face the problem of the degradation of a thermal inkjet printhead.

SUMMARY OF THE INVENTION

Surprisingly, the Applicant has noticed that a thermal inkjet printhead loaded with a biological fluid (i.e., an aqueous solution comprising DNA, proteins, viral material, cells, tissues, etc.) and used for producing a microarray, shows a behavior substantially different from that showed when it is loaded with an ink conventionally employed for printing an image onto a paper support.

In particular, the Applicant has observed that a conventional printhead loaded with a biological fluid and supplied with the energy values above defined with reference to the prior art rapidly damages.

In fact, by examining the printhead after a deposition process of a biological fluid onto the surface of a substrate, the Applicant has noticed a layer of residual biological products being present on the surface of the heating element. This results in a rapid damage of the printhead, as described above.

It has to be noticed that biological fluids, once loaded into a printhead, can no more be used, since it is difficult to maintain unchanged their biological activity. Therefore, if the printhead rapidly damages, the biological fluid contained therein, and that has not yet been deposited onto the surface of the substrate, is inevitably wasted.

The biological fluids used for producing microarrays, e.g. DNA and protein containing fluids, are very expensive, whereby their waste is undesirable.

Further, it is known that a microarray must be ordered, so to properly operate as a diagnostic tool. A microarray is referred to as ordered when the spots of biological fluid are arranged on the substrate in a precise and accurate manner along rows and columns. Any smears, although minima, of a spot are not admissible, since they could contaminate the reading of an adjacent spot.

Moreover, spots of biological fluid must be homogeneous. Spots having different shapes or densities, even if they contain the same number of molecules of biological fluid, would generate signals having different intensity, thus compromising the reproducibility of the biological analysis carried out with the microarrays. Therefore, the printhead has to eject stable drops of biological fluid during all its operation.

Therefore, the Applicant has faced the problem to provide a method and an apparatus for depositing a biological fluid onto the surface of a substrate by using a thermal bubble-jet printhead, which are capable of overcoming at least one of the above mentioned drawbacks.

In particular, the Applicant has faced the problem to provide a method and an apparatus for depositing a biological fluid onto the surface of a substrate by using a thermal bubble-jet printhead, which are capable of increasing the lifetime of the printhead and ejecting and subsequently depositing stable drops for a time sufficient to exhaust the whole biological fluid loaded into the printhead.

Surprisingly, the Applicant has noticed that a thermal printhead loaded with a biological fluid, and used for depositing a biological fluid onto the surface of a substrate thereby producing a microarray, presents an increased lifetime when it is supplied with an energy E greater than that conventionally used in the art of the thermal inkjet printing technique.

Moreover, surprisingly, the Applicant has observed that a printhead supplied with an energy E greater than that conventionally used in art of the thermal inkjet printing technique is capable of ejecting stable drops during all the time required for exhausting the quantity of biological fluid loaded into the printhead.

Advantageously, this allows to obtain functionally performing microarrays, i.e. microarrays capable of guaranteeing a high reproducibility level of the biological analysis carried out through them, meanwhile avoiding the waste of expensive biological fluids.

According to a first aspect the present invention relates to a method for depositing at least one biological fluid onto a surface (12) of a substrate (10), said method comprising the steps of:

providing at least one thermal bubble-jet printhead (T1, T2, T3) loaded with at least one biological fluid;

positioning said at least one printhead (T1, T2, T3) next to said substrate (10); and supplying energy to said at least one printhead (T1, T2, T3) thereby depositing said at least one biological fluid onto said surface (12);

characterized in that said at least one printhead (T1, T2, T3) is supplied with an energy E such that $$E > 1.6 * E_{th}$$

where $E_{th}$ is the threshold energy of the printhead for said biological fluid.

Preferably, said at least one printhead (T1, T2, T3) is supplied with an energy E, such that $1.6*E_{th} < E \leq 3.0*E_{th}$, more preferably with an energy E such that $1.8*E_{th} \leq E \leq 2.2*E_{th}$.

Advantageously, said at least one printhead (T1, T2, T3) ejects a total number of drops ranging from $0.5 \times 10^6$ to $2 \times 10^6$.

Preferably, the deposition of said at least one biological fluid onto said surface (12) is repeated at least two times, more preferably, a number of times ranging from 2 to 100, most preferably ranging from 2 and 30. More particularly, the time period between two subsequent depositions is ranging from 5 to 600 seconds, preferably from 5 to 60 seconds.

Preferably, the biological fluid comprises at least one biological substance dissolved in an aqueous solvent comprising more than 50% by weight, preferably more than 70% by weight, and most preferably more than 80% by weight relative to the total weight of said biological fluid of water.

Advantageously, the biological fluid comprises organic fluids, protein solution, tissue and cell lysates, nucleic acid solutions, nucleic acid analogue solutions, and the like.

In a second aspect, the present invention relates to an apparatus (DA) for depositing at least one biological fluid onto a surface (12) of a substrate (10), said apparatus (DA) comprising:

a processing device (PD);

a thermal bubble-jet printhead assembly (PA) including at least one printhead (T1, T2, T3), wherein the at least one printhead (T1, T2, T3) is at least partially loaded with said at least one biological fluid;

a controller (CTRL) connected to said processing device (PD);

a power supply (PS) responsive to the controller (CTRL) for supplying energy to said thermal bubble-jet printhead assembly (PA) so that said at least one biological fluid is deposited onto said surface (12);

characterized in that said power supply (PS) supplies said at least one printhead (T1, T2, T3) with an energy Ei ($E_1$, $E_2$, $E_3$) such that $$E_i > 1.6 * E_{thi}$$

where $E_{thi}$ is the threshold energy of said at least one printhead (T1, T2, T3) for said at least one biological fluid.

In a third aspect, the present invention relates to a microarray (MA) comprising a substrate (10) with a substrate surface (12) and a plurality of biological fluid spots (S1, S2, ... Sn), wherein said microarray (MA) is obtained by carrying out a depositing method as described above.

BRIEF DESCRIPTION OF THE DRAWINGS

The present invention will be better understood by reading the following detailed description, given by way of non limitative example, to be read by referring to the accompanying drawings, wherein.

DETAILED DESCRIPTION OF PREFERRED EMBODIMENTS OF THE INVENTION

Therefore, according to a first aspect, the present invention provides a method for depositing at least one biological fluid onto a surface of a substrate, the method comprising the steps of (i) providing at least one thermal bubble-jet printhead loaded with a respective biological fluid, (ii) positioning the printhead next to the substrate, and (iii) supplying energy to the printhead, thereby depositing the biological fluid onto the substrate.

The printhead is supplied with an energy E such that:

$$E > 1.6 * E_{th}$$

where $E_{th}$ is the threshold energy of the printhead. The symbol * is used in the present description and in the following claims for indicating a multiplying operation. Therefore, the above formula means that the supplied energy E is higher than 1.6 times the threshold energy $E_{th}$.

Preferably, the supply energy E ranges between $1.6*E_{th}$ and $3*E_{th}$. More preferably, the supply energy E ranges between $1.8*E_{th}$ and $2.2*E_{th}$.

Figure 1A:
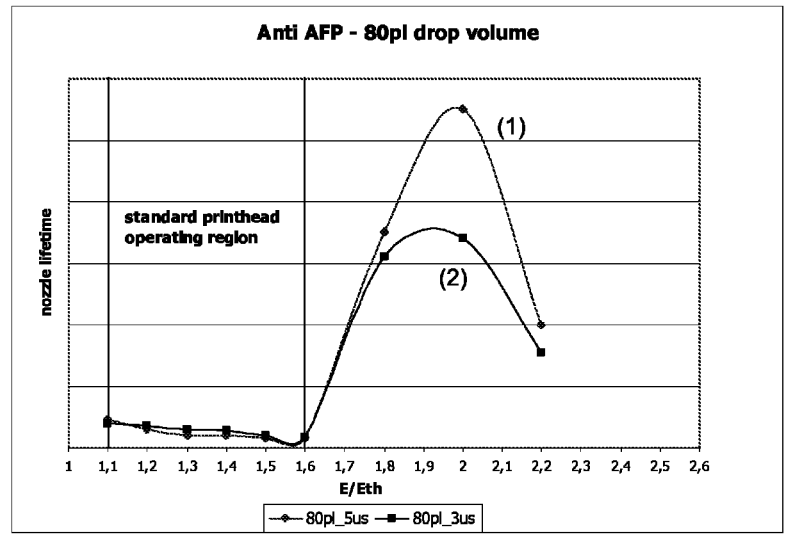
FIGS. 1a and 1b show graphics of the nozzle lifetime by using the Polyclonal Rabbit Anti-Human Alpha-1-Fetoprotein.
Figure 1B:
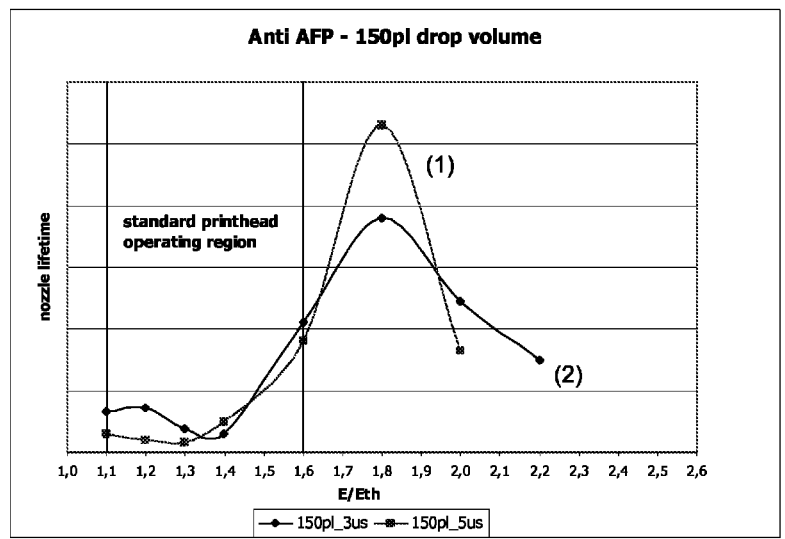

FIGS. 1a and 1b show the graphic of the lifetime of a thermal bubble-jet printhead loaded with a biological fluid versus the supply energy E to threshold energy $E_{th}$ ratio $E/E_{th}$ for two different drop volumes, namely 80 pl (FIG. 1a) and 150 pl (FIG. 1b). The printhead was an Olivetti thermal printhead having 260 nozzles, which was loaded with a commercial polyclonal antibody, namely the Polyclonal Rabbit Anti-Human Alpha-1-Fetoprotein (DAKO A0008-0.25 mg/ml), diluted in 0.01 M phosphate buffer, 0.0027 M potassium chloride and 0.137 M sodium chloride, pH 7.4@25° C. (phosphate buffer solution—Sigma Aldrich P4417). Preferably, the polyclonal antibody was deposited onto glass slides (1 inch by 3 inches) treated on their surface thereby exposing positive charges (Superfrost Plus Menzel—217658 Clinilab).

Figure 2A:
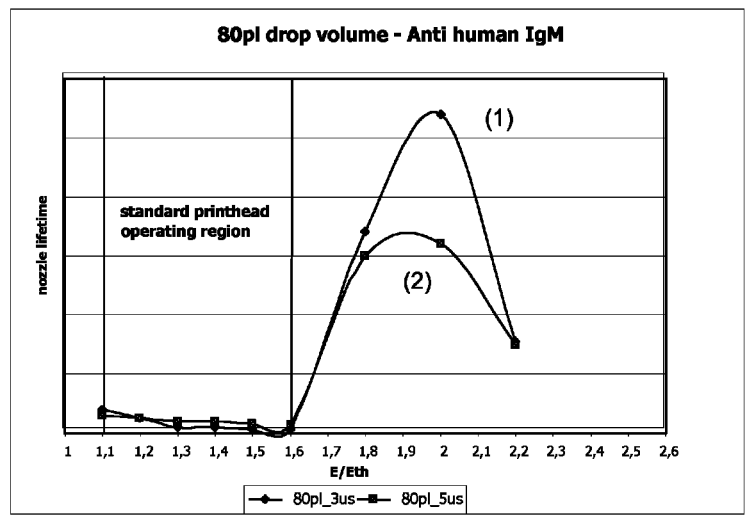
FIGS. 2a and 2b show graphics of the nozzle lifetime by using the Polyclonal Rabbit Anti-Human IgM.
Figure 2B:
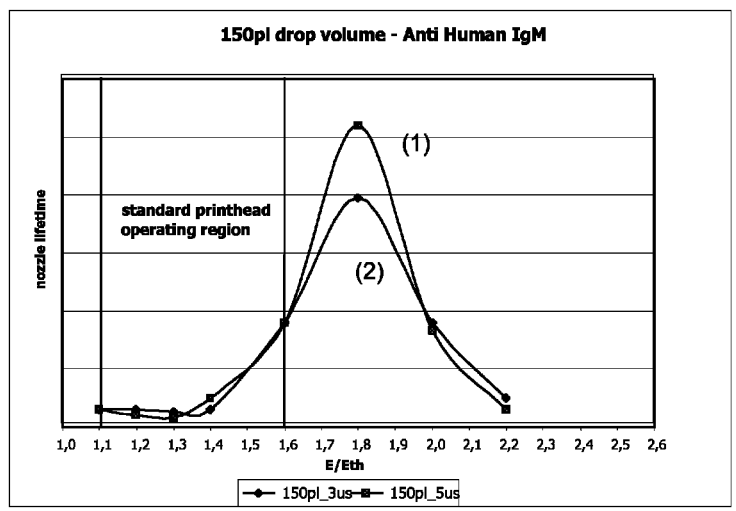

Similarly, FIGS. 2a and 2b show the graphic of the lifetime of a thermal bubble-jet printhead loaded with a biological fluid versus the supply energy E to threshold energy $E_{th}$ ratio $E/E_{th}$ for two different drop volumes, namely 80 pl (FIG. 2a) and 150 pl (FIG. 2b). The printhead was an Olivetti thermal printhead having 260 nozzles; which was loaded with a commercial polyclonal antibody, namely the Polyclonal Rabbit Anti-Human IgM (DAKO A0425, 0.25 mg/ml), diluted in 0.01 M phosphate buffer, 0.0027 M potassium chloride and 0.137 M sodium chloride, pH 7.4@25° C. (phosphate buffer solution—Sigma Aldrich P4417).

Figure 3A:
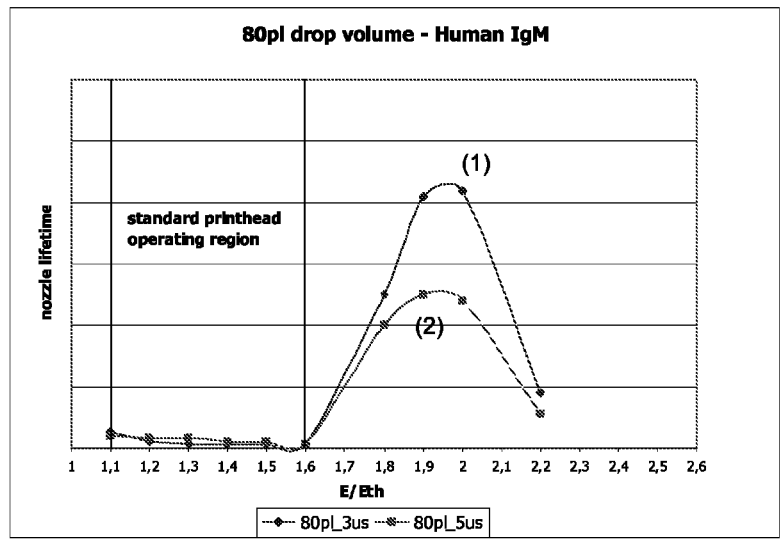
FIGS. 3a and 3b show graphics of the nozzle lifetime by using the IgM from Human Serum.
Figure 3B:
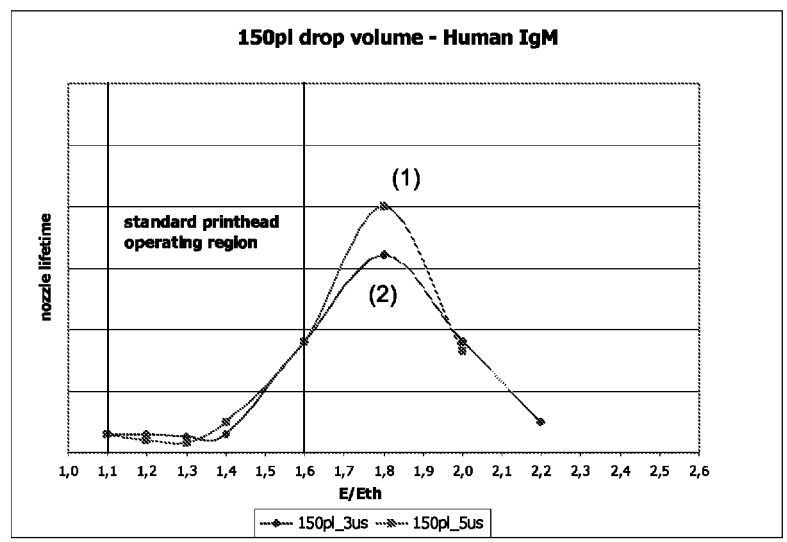
Figure 4:
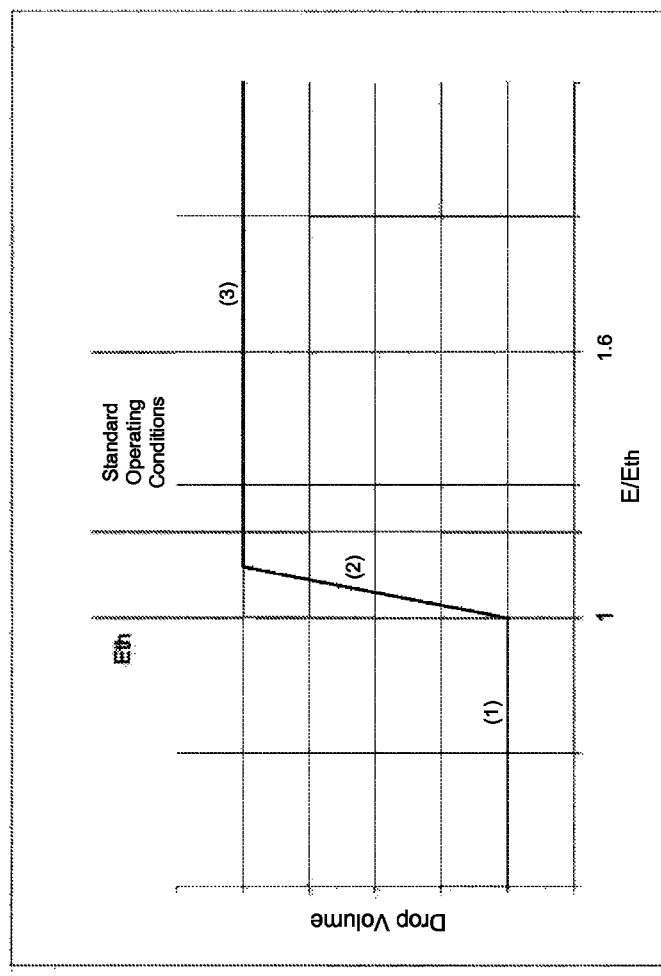
FIG. 4 shows a graphic of the relationship between the volume of an ejected biological fluid drop and the supply energy to threshold energy ratio $E/E_{th}$ for a printhead.

Further, FIGS. 3a and 3b show the graphic of the lifetime of a thermal bubble-jet printhead loaded with a biological fluid versus the supply energy E to threshold energy $E_{th}$ ratio $E/E_{th}$ for two different drop volumes, namely 80 pl (FIG. 3a) and 150 pl (FIG. 3b). The printhead was an Olivetti thermal printhead having 260 nozzles, which was loaded with a commercial polyclonal antibody, namely the IgM from Human Serum, 0.25 mg/ml, (SIGMA ALDRICH 18260), diluted in 0.01 M phosphate buffer, 0.0027 M potassium chloride and 0.137 M sodium chloride, pH 7.4@25° C. (phosphate buffer solution—Sigma Aldrich P4417).

The printhead was then supplied with a pulse energy $$E = (V^2 * t)/R$$

where V is the voltage applied to the printhead, or driving voltage, t is the length of a pulse and R is the resistance of the heating element of the printhead. In particular, in the FIGS. 1a, 1b, 2a, 2b, 3a, and 3b, curve (1) relates to a printhead supplied with pulses having a length of 3 microseconds, whereas curve (2) relates to a printhead supplied with pulses having a length of 5 microseconds. The Applicant noted that at constant pulse length (5, 3 or 2 μs) and drop volume (80 or 150 pl), the threshold voltage (V) did not change by using different biological fluids, as clearly showed in the Table 1 below.

|  | 80 pl | | | 150 pl | | |
| --- | --- | --- | --- | --- | --- | --- |
|  | 5 μs | 3 μs | 2 μs | 5 μs | 3 μs | 2 μs |
| DAKO A0008 | 11.4 | 14.0 | 16.7 | 14.8 | 18.2 | 22.5 |
| DAKO A0425 | 11.4 | 14.0 | 16.7 | 14.8 | 18.2 | 22.5 |
| SIGMA ALDRICH I8260 | 11.4 | 14.0 | 16.7 | 14.8 | 18.2 | 22.5 |

As it can be noticed from the figures, for values of supply energy E within the range from $1.1*E_{th}$ to $1.6*E_{th}$, the lifetime of the printhead is substantially null. For values of supply energy $E>1.6*E_{th}$, the printhead lifetime rapidly increases, and reaches its peak value for $1.8*E_{th} \leq E \leq 2.0*E_{th}$. Subsequently, it gradually decreases.

Figure 5:
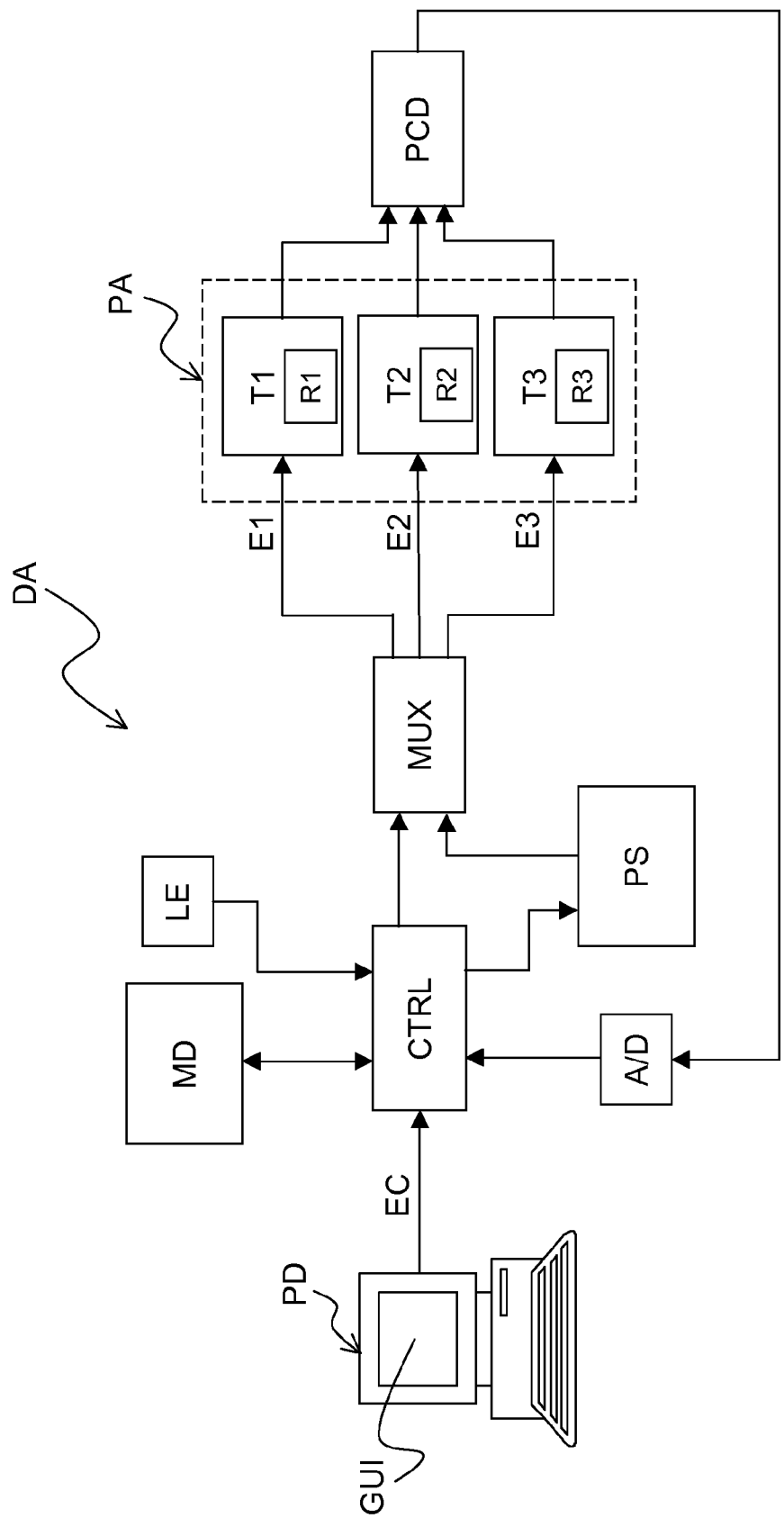
FIG. 5 schematically shows an apparatus for depositing a biological fluid onto the surface of a substrate according to one embodiment of the present invention.

As a result, surprisingly, the printhead loaded with a biological fluid, in place of ink, presents an increased lifetime when supplied with an energy E greater than that conventionally used in the art of the thermal inkjet printing technique.

By using the same energy values as described above for different proteins, aqueous solutions of oligonucleotides have been printed with the same Olivetti thermal printhead having 260 nozzles. Similarly, there has been no problem of short printhead lifetime. In this particular case, the Applicant noted that the standard printing conditions (20%-60% over the threshold energy) can be usefully employed for oligonucleotides solutions. For example 12 million drops of 10 mMol solution of amino-modified 25-mer oligoes with and without cyanine modifications, have been successfully printed by using driving energy values 20% and 120% over the threshold energy. The oligoes employed were those having the following formulas, manufactured by Sigma Genosys:

```
1 HPLC purified
Cy5-TGC CAA CGT GTC AGT GGT GGA CCT G-Ammine C7

2 HPLC purified
Cy3-TGC CAA CGT GTC AGT GGT GGA CCT G-Ammine C7

3 HPLC purified
TGC CAA CGT GTC AGT GGT GGA CCT G-Ammine C7
```

With reference now to the total number of drops ejected through the nozzles, the Applicant has found that for values of the supply energy E within the range from $1.1*E_{th}$ to $1.6*E_{th}$, a printhead loaded with a biological fluid ejects a total number of drops of about $2\times10^4$-$6\times10^4$, whereas within the energy range from $1.8*E_{th}$ to $2.2*E_{th}$ determined as being advantageous by the present invention, the total number of ejected drops increases to $0.5\times10^6$-$2\times10^6$.

Advantageously, the method and apparatus of the present invention allows to deposit a wide range of biological fluid for testing and examination purpose, such as for example, organic fluids, protein solution (fibrous and globular proteins, immunoglobulines, hormones, enzymes, antibodies, antigenes, allergens, viral capsid material), tissue and cell lysates, nucleic acids, (DNA, cDNA, RNA, tRNA, mRNA, plasmids, oligonucleotides), nucleic acid analogues and the like.

FIG. 4 shows the relationship between the volume of a drop of biological fluid ejected through a printhead and the ratio $E/E_{th}$ between the energy supplied to the printhead and the threshold energy of the printhead.

It is noticed that, when the printhead is loaded with a biological fluid, the drop volume has a plot similar to that previously described with reference to a conventional thermal inkjet printhead.

More specifically, for values of energy E below the threshold energy $E_{th}$ (length (1) of the curve of FIG. 1; $E/E_{th}<1$) any drop is not ejected through the nozzles of the printhead. When the threshold energy $E_{th}$ is exceeded instable drops are ejected (length (2) of the curve of FIG. 2, $E/E_{th}>1$) which subsequently become stable (length (3) of the curve of FIG. 2). Therefore, the graphic of FIG. 4 shows that for values of the supply energy $E>1.6*E_{th}$, drops ejected through the printhead loaded with a biological fluid remain stable.

In particular, the portion (2) of the curve is referred to as the drop instability zone, i.e. a zone where the drop volume can significantly vary upon small variations of the energy E, whereas the portion (3) of the curve is referred to as the drop stability zone, i.e. a zone where the drop volume remains substantially constant upon small, and even high, variations of the energy E.

The Applicant believes that a possible explanation of the above described surprising phenomena can be found in a greater cleaning of the heating element of the thermal printhead.

More specifically, the higher the energy supplied to the printhead, the higher the temperature reached by the heating element, and consequently, during operation, the higher the temperature of the heating element surface contacting the biological fluid to be deposited onto the substrate. As a result, the layer of residual biological products grown on the surface of the heating element changes its chemical-physical properties, making easier the continuous peeling of the heating element surface, due to the extremely fast bubble collapse that partially removes the layer itself.

Preferably, the drops of biological fluid, namely polyclonal antibody, were deposited onto glass slides by using a so called multi-deposition technique. This multi-deposition technique consists of repeating more times a predetermined printing pattern on the same area of the substrate, i.e. overlapping the same deposition pattern on the same substrate. Preferably, the deposition pattern is repeated from 2 to 100 times, more preferably from 2 to 30 times on the same area.

Advantageously, the multi-deposition technique allows to deposit onto the substrate a predetermined amount of biological fluid by using small drop volumes, which drop volumes would be otherwise insufficient to deposit enough biological fluid in a single deposition. Preferably, between successive depositions a pause is carried out, which typically ranges from 5 to 600 seconds, preferably from 5 to 60 seconds. The pause allows the previously deposited biological material to dry, even partially, thereby improving successive depositions.

Often, during the deposition of a biological fluid, one or more nozzles of the printhead can clog. This is caused by the crystallization of salts typically present within the biological fluid, owing to a fast evaporation of the biological fluid close to the nozzles.

On the other hand, during the process of producing a microarray, it is particularly important to guarantee a continuous and regular operation of the nozzles, since the spots have to contain a constant amount of biological fluid and to show a well defined geometry.

As a result, the nozzle occlusion can cause a detriment of the microarray performance. This is because if nozzles partially occlude, the size of the ejected drops could vary and/or the drops could be wrongly directed onto the substrate. In the worst case, the nozzles could totally occlude and thus no drop would be ejected therefrom.

To reduce and slow down this undesired phenomenon, the biological fluid is preferably added with suitable substances, such as glycerol, polyethylene glycol, mineral oil, and the like.

Advantageously, the additives cause the vapor pressure of the biological fluid to decrease, thereby limiting its evaporation. This reduces the liquid evaporation at the orifice-air interface, so minimizing the clogging phenomenon.

The nozzle occlusion is otherwise due to particles contained in the biological fluid or to clusters of biological molecules having size comparable with the nozzle diameter.

To overcome this drawback, the biological fluid is advantageously filtered before loading it into the printhead.

FIG. 5 schematically shows an embodiment of an apparatus for depositing a biological fluid onto the surface of a substrate according to the present invention.

The depositing apparatus, generally designated as DA, comprises a processing device PD connected to a controller CTRL. Preferably, the processing device PD is a computer provided with a graphical user interface GUI.

The controller CTRL is connected to a moving device MD, a power supply PS and a multiplexer MUX, for mechanically and electrically driving a thermal bubble-jet printhead assembly PA, comprising a plurality of printheads T1, T2, T3, with respect to the substrate. Each printhead is provided with a respective heating element R1, R2, R3.

For sake of simplicity, the printhead assembly PA of the depositing apparatus DA is represented as comprising only three printheads T1, T2, T3. Obviously, this is merely exemplary, since the printhead assembly PA can comprise any number of printheads.

Preferably, each printhead T1, T2 and T3 is at least partially loaded with a different biological fluid. It is assumed, for example, that the each printhead T1, T2, T3 is loaded with a different commercial polyclonal antibody. This advantageously allows to deposit spots of different biological fluids onto the same substrate.

In use, the operator of the depositing apparatus DA inputs a plurality of operative parameters by means of the graphical user interface GUI of the computer.

These operative parameters may comprise an input image file representing the depositing pattern of one or more biological fluids on the substrate. Moreover, the operative parameters may comprise the coordinates x, y, z of the starting and ending points of a predetermined deposition range, generally corresponding to the size of the substrate.

Moreover, for each printhead T1, T2, T3, the operative parameters may comprise information related to the total volume of biological fluid to be ejected and information related to the thermodynamic and fluidodynamic characteristics of the biological fluid contained therein, e.g. boiling point, surface tension, density, viscosity, and the like. Besides, the operative parameters may comprise parameters related to how the printheads are driven, such as driving voltage, pulse length, and operating frequency.

The processing device PD preferably translates the input image file in a sequence of bits and transmits them, together with at least one of the operative parameters above listed, to the controller CTRL, e.g. by means of a Ethernet connection EC.

The controller CTRL is suitable for cooperating with the moving device MD and the multiplexer MUX for translating the printheads T1, T2, T3 with respect to the substrate. More preferably, the printheads are translated while the substrate is maintained fixed. The movement can be performed along one, two or three axes orthogonal one to another. Typically, the movement is performed along two or three axis.

More specifically, the controller CTRL transmits to the moving device MD the coordinates x, y, z of the starting and ending points of the printing range received by the processing device PD. Preferably, the moving device MD generates mechanical driving signals, preferably translation signals, and transmits them to the controller CTRL. The controller CTRL transmits the mechanical driving signals to the printheads T1, T2, T3 through the multiplexer MUX. In this way, each printhead T1, T2, T3 translates with respect to the substrate.

Preferably, the depositing apparatus PA includes an encoder, e.g. a linear optical encoder LE, connected to the controller CTRL and adapted to check the instantaneous position of each printhead T1, T2, T3 and to synchronize the drop ejection with the printhead translation motion.

Further, the controller CTRL is suitable for cooperating with the power supply PS in order to supply the printheads T1, T2, T3 with a respective energy $E_1$, $E_2$ and $E_3$, thereby ejecting a drop of biological fluid. Specifically, the energy $E_1$, $E_2$ and $E_3$ are such that:

$$E_1 > 1.6 * E_{th1}$$

$$E_2 > 1.6 * E_{th2}$$

$$E_3 > 1.6 * E_{th3}$$

where $E_{th1}$, $E_{th2}$, $E_{th3}$, are the threshold energies of the printheads T1, T2 and T3, which, as described above, depend on the fluidodynamic characteristics, e.g. boiling point, surface tension, density and viscosity, of the biological fluid contained in each printhead T1, T2, T3.

More specifically, the controller CTRL, based on the operative parameters (e.g. total volume of biological fluid to be ejected and driving voltage of each printhead) received by the processing device PD, drives the power supply PS thereby generating the above defined values of energy $E_1$, $E_2$ and $E_3$. The power supply PS, in turn, supplies each printhead T1, T2, T3 with the respective energy $E_1$, $E_2$, $E_3$ through the multiplexer MUX.

Advantageously, the energies $E_1$, $E_2$, $E_3$ are selected to provide the maximum lifetime of the printheads and to allow the whole ejection of all the biological fluid contained inside the printhead, thereby avoiding any expensive waste thereof.

The Applicant has noticed that the threshold energies of the biological fluids substantially based on an aqueous media do not substantially change. More in particular, a biological fluid comprising at least one biological substance dissolved in an aqueous solvent comprising more than 50% by weight (relative to the total weight of said biological fluid) of water shows a threshold energy which value is substantially independent from the biological substance contained in it. Preferably, the biological fluid comprises more than 70% by weight, and most preferably more than 80% by weight of water relative to the total weight of said biological fluid.

The Applicant has found that the above mentioned finding allows to employ a single, pre-determined threshold energy for all the biological fluids to be spotted without the need of adapting each printheads with a respective energy.

On the other hand, the capability of the controller CTRL of cooperating with the power supply PS in order to supply the printheads T1, T2, T3 with a respective energy $E_1$, $E_2$ and $E_3$, can be useful when one or more of the printheads T1, T2, T3 contain a fluid other than the biological fluid, such as, for example, an ink for printing information data about the specific probe or assay on a portion of the surface of a substrate.

In one preferred embodiment of the present invention, there is provided an arrangement for checking the driving voltage at each heating element R1, R2, R3 of the printheads T1, T2 and T3. Such an arrangement may comprise a printhead checking device PCD. It receives in input the actual voltage across the printheads T1, T2, T3 and, for each printhead T1, T2, T3, outputs an analog electric signal indicating the voltage of the respective printhead T1, T2 and T3. Each analog electric signal is thus transmitted to an analog/digital converter A/D, which generates a respective digital output, which is in turn transmitted to the controller CTRL. The controller CTRL compares the received information and provides the comparison result to the power supply PS. In turn, the power supply PS properly supplies, by means of the multiplexer MUX, each printhead with the right energy $E_1$, $E_2$, $E_3$. Therefore, in other words, there is provided a feedback, based on the actual resistive characteristics of each heating element, for properly feeding the printheads.

Although, the analog signal which outputs from the printhead checking device PCD is transmitted to the controller CTRL on a dedicated link, it is merely exemplary, because, the analog signal could be transmitted on the same link connecting the multiplexer MUX to the controller CTRL. In this latter case, the link would be a bidirectional link.

Figure 6:
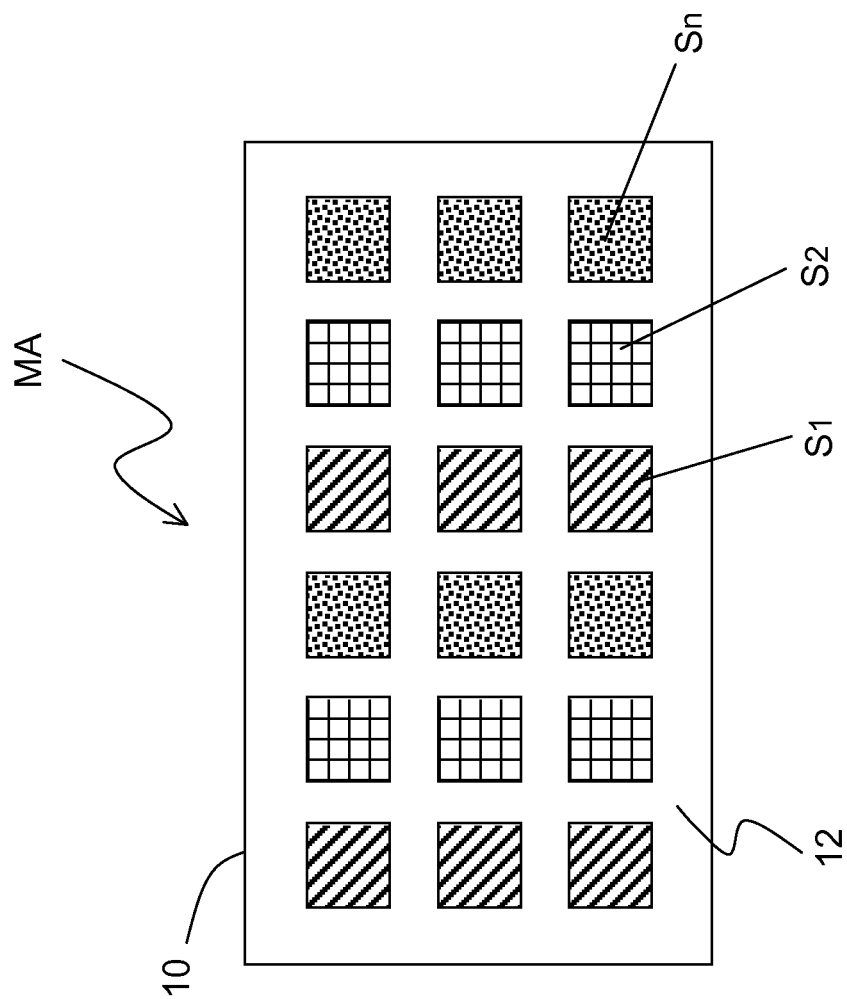
FIG. 6 shows a schematic plant view of a microarray according to one embodiment of the present invention.

FIG. 6 schematically shows an embodiment of a microarray obtained by carrying out the depositing method of the invention. The microarray, generally designed as MA, comprises a substrate 10 having a surface 10 on which a plurality of spots S1, S2, . . . Sn of one or more biological fluids is deposited.

Advantageously, the depositing apparatus DA of the present invention, allows to supply each printhead with an energy suitable for providing the maximum lifetime of the printheads and to allow the whole ejection of all the biological fluid contained inside the printhead, thereby avoiding an expensive waste thereof.

Further advantageously, the depositing apparatus DA allows to eject and deposit stable drops of a plurality of biological fluids, thus obtaining a microarray provided with ordered and homogeneous spots.

The invention claimed is:

1. A method for depositing at least one biological fluid onto a surface of a substrate, said method comprising the steps of:
    a) loading at least one thermal bubble-jet printhead with at least one biological fluid;
    b) positioning said at least one printhead next to said substrate; and
    c) depositing said at least one biological fluid onto said surface by supplying energy E to said at least one printhead, wherein $$E > 1.6 * E_{th}$$

and $E_{th}$ is the threshold energy of the printhead for said biological fluid.

2. The method according to claim 1, wherein the depositing step includes supplying said at least one printhead with an energy E, such that $1.6*E_{th} < E \leq 3.0*E_{th}$.

3. The method according to claim 1, wherein the depositing step includes supplying said at least one printhead with an energy E such that $1.8*E_{th} < E \leq 2.2*E_{th}$.

4. The method according to claim 1, wherein the depositing includes ejecting from said at least one printhead total number of drops ranging from about $0.5 \times 10^6$ to about $2 \times 10^6$.

5. The method according to claim 1, further comprising repeating the step of depositing of said at least one biological fluid onto said surface at least two times.

6. The method according to claim 5, wherein said depositing step is repeated a number of times ranging from 2 to 100.

7. The method according to claim 5, wherein said depositing step is repeated a number of times ranging from 2 and 30.

8. The method according to claim 5, wherein the time period between two subsequent deposits ranges from about 5 to about 600 seconds.

9. The method according to claim 5, wherein the time period between two subsequent deposits ranges from about from 5 to about 60 seconds.

10. The method according to claim 1, further comprising filtering said at least one biological fluid before said loading step (a).

11. The method according to claim 1, wherein the loading step includes loading said at least one thermal bubble-jet printhead with a biological fluid that comprises at least one biological substance dissolved in an aqueous solvent comprising more than 50% by weight of water relative to the total weight of said biological fluid.

12. The method according to claim 1, wherein said biological fluid comprises at least one of organic fluids, protein solution, tissue and cell lysates, nucleic acid solutions, or nucleic acid analogue solutions.

13. An apparatus for depositing at least one biological fluid onto a surface of a substrate, said apparatus comprising:
    a processing device;
    a thermal bubble-jet printhead assembly including at least one printhead, wherein the at least one printhead is at least partially loaded with said at least one biological fluid;
    a controller connected to said processing device;
    a power supply responsive to the controller for supplying energy to said thermal bubble-jet printhead assembly so that said at least one biological fluid is deposited onto said surface, wherein said power supply supplies said at least one printhead with an energy Ei such that $$E_i > 1.6 * E_{thi}$$

where $E_{thi}$ is the threshold energy of said at least one printhead for said at least one biological fluid.

14. The apparatus according to claim 13, wherein said at least one printhead is supplied with an energy $E_i$, such that $$1.6*E_{thi} < E_i \leq 3.0*E_{thi}.$$

15. The apparatus according to claim 13, wherein said at least one printhead (T1, T2, T3) is supplied with an energy $E_i$, such that $$1.8*E_{thi} < E_i \leq 2.2*E_{thi}.$$

16. A microarray comprising a substrate with a substrate surface and a plurality of biological fluid spots, wherein said microarray is obtained by carrying out a depositing method according to claim 1.

17. A method of creating a microarray of a plurality of biological fluid spots on a surface of a substrate, comprising utilizing the apparatus according to claim 13.

* * * * *

UNITED STATES PATENT AND TRADEMARK OFFICE
CERTIFICATE OF CORRECTION

| | | |
|---|---|---|
| PATENT NO. | : 8,993,040 B2 | Page 1 of 1 |
| APPLICATION NO. | : 13/266913 | |
| DATED | : March 31, 2015 | |
| INVENTOR(S) | : G. Mabritto et al. | |

It is certified that error appears in the above-identified patent and that said Letters Patent is hereby corrected as shown below:

Title Page, at Item (73) Assignee, of the printed patent, "SICPA Holding SA" should read -- SICPA HOLDING SA --.

Title Page, Abstract, column 2, lines 3 and 4, please change "bubble jet" to -- bubble-jet --.

Claims

Column 11, line 46 (claim 3, line 3) please change "$<E\leq$" to -- $\leq E \leq$ --.

Signed and Sealed this
Ninth Day of February, 2016

Michelle K. Lee
*Director of the United States Patent and Trademark Office*